United States Patent [19]

Habib et al.

[11] 4,352,947
[45] Oct. 5, 1982

[54] PROCESS FOR PRODUCING ETHANOL

[75] Inventors: Mohammad M. Habib, Allison Park; Wayne R. Pretzer, Gibsonia, both of Pa.

[73] Assignee: Gulf Research & Development Company, Pittsburgh, Pa.

[21] Appl. No.: 289,406

[22] Filed: Aug. 3, 1981

[51] Int. Cl.³ ............................................. C07C 29/00
[52] U.S. Cl. .................................................. 568/902
[58] Field of Search ......................................... 568/902

[56] References Cited

U.S. PATENT DOCUMENTS

| 4,233,466 | 11/1980 | Fiato ................................... | 568/902 |
| 4,239,924 | 12/1980 | Pretzer et al. ....................... | 568/902 |
| 4,262,154 | 4/1981 | Gane et al. .......................... | 568/902 |

FOREIGN PATENT DOCUMENTS

| 2053915 | 2/1981 | United Kingdom ................. | 568/902 |

OTHER PUBLICATIONS

CRC Handbook of Chemistry and Physics, 54th edition, 1973–1974, inside front cover or inside back cover.

*Primary Examiner*—Joseph E. Evans
*Attorney, Agent, or Firm*—Deane E. Keith; Forrest D. Stine; Joseph J. Carducci

[57] ABSTRACT

A process for selectively producing alcohols, particularly ethanol, which comprises introducing into a reaction zone (1) methanol, (2) carbon monoxide, (3) hydrogen, (4) cobalt, (5) iodine, (6) ruthenium and (7) a ligand containing atoms from Group VA of the Periodic Table separated by a sterically constrained carbon-carbon bond, and then subjecting the contents of said reaction zone to an elevated temperature and an elevated pressure for a time sufficient to convert methanol to said ethanol.

41 Claims, No Drawings

PROCESS FOR PRODUCING ETHANOL

BACKGROUND OF THE INVENTION

1. Field of the Invention

This invention is directed to a process for selectively producing ethanol, which comprises introducing into a reaction zone (1) methanol, (2) carbon monoxide, (3) hydrogen, (4) cobalt, (5) iodine, (6) ruthenium and (7) a ligand containing atoms from Group VA of the Periodic Table separated by a sterically constrained carbon-carbon bond, and then subjecting the contents of said reaction zone to an elevated temperature and an elevated pressure for a time sufficient to convert methanol to said ethanol.

2. Description of the Invention

In our U.S. patent application Ser. No. 289,404, entitled "Process for Producing Aldehydes", filed concurrently herewith, we disclosed and claimed a process for selectively producing aldehydes which comprised introducing into a reaction zone (1) methanol, (2) carbon monoxide, (3) hydrogen, (4) cobalt, (5) iodine and (6) a ligand containing atoms from Group VB of the Periodic Table separated by a sterically constrained carbon-carbon bond, and then subjecting the contents of said reaction zone to an elevated temperature and an elevated pressure for a time sufficient to convert methanol to said aldehydes.

SUMMARY OF THE INVENTION

We have found that if we introduce into a reaction zone (1) methanol, (2) carbon monoxide, (3) hydrogen, (4) cobalt, (5) iodine, (6) ruthenium and (7) a ligand containing atoms from Group VB of the Periodic Table separated by a sterically constrained carbon-carbon bond, while controlling the proportion of the reaction components and the reaction parameters, we can obtain a reaction product predominating in ethanol, including compounds convertible thereto. By "compounds convertible thereto" we mean to include acetaldehyde, diethylether and ethylacetate. In general the homologated product will contain at least about 40 mol percent, especially from about 45 to about 90 mol percent of ethanol and compounds convertible thereto. The ethanol content of the homologated product will be at least about 25 mol percent, especially from about 30 to about 80 mol percent. In fact, the amount of realizable alcohols in the homologated product will be at least about 50 mol percent, especially from about 60 to about 90 mole percent. The compounds referred to above that can be converted to ethanol or to alcohols in general can be converted thereto by any known or suitable process, for example, by hydrolysis; that is, contacting a precursor thereof with water, with or without an acid (sulfuric) or a basic (sodium hydroxide) catalyst, or by hydrogenation with hydrogen in the presence of a catalyst, such as cobalt, nickel or ruthenium.

As noted, the ligand used herein contains atoms from Group VA of the Periodic Table. By "Group VA atoms" we mean to include nitrogen, phosphorus and arsenic. By a "sterically constrained carbon-carbon bond" we mean to include a carbon-carbon bond of an organic divalent radical in which the radical centers are located on adjacent carbon atoms and in which the bond axis of these adjacent carbon atoms is inhibited from rotating by either bond unsaturation or by their incorporation into an alicyclic ring system. By "bond unsaturation" we mean to include an alkenylene bond, such as:

and an 1,2-arylene bond, such as:

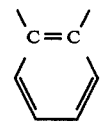

or an acetylenic bond such as —C≡C— wherein any of the above-defined R substituents can be hydrogen, a hydrocarbyl, such as defined hereinafter, a halogen, such as chlorine or bromine, a sulfur-containing substituent, such as a sulfonato group, a nitrogen-containing substituent, such as a nitro group or an amino group, an oxygen-containing substituent, such as a hydroxyl group, etc. By "alicyclic ring system" we mean to include an aliphatic ring system comprising a three- to eight-membered ring, such as:

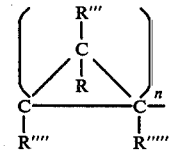

wherein n=1, 2, 3, 4, 5, or 6, and any of the above-defined R groups can be similar to R' and R''.

Especially preferred ligands for use herein can be defined by the following formula:

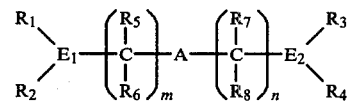

wherein $R_1$, $R_2$, $R_3$ and $R_4$ are either alike or different members selected from the group consisting of alkyl radicals having from one to 24 carbon atoms, preferably from two to 10 carbon atoms; aryl radicals having from six to 20 carbon atoms, preferably from six to 10 carbon atoms; alkenyl radicals having from two to 30 carbon atoms, preferably from two to 20 carbon atoms; cycloalkyl radicals having from three to 40 carbon atoms, preferably from three to 30 carbon atoms; and aralkyl and alkaryl radicals having from six to 40 carbon atoms, preferably from six to 30 carbon atoms, preferably aryl or alkyl; $R_5$, $R_6$, $R_7$ and $R_8$ are either alike or different members selected from $R_1$, $R_2$, $R_3$ and $R_4$, defined above, and hydrogen, preferably hydrogen or alkyl; $E_1$ and $E_2$ the same or different, can be phosphorus or arsenic, preferably with $E_1$ being phosphorus and $E_2$ being arsenic, most preferably with each of $E_1$ and $E_2$ being phosphorus; and m and n being integers ranging from 0 to 2, preferably from 0 to 1, provided that m+n=0–4, preferably 0–2; and A can be an organic divalent radical in which the radical centers are located on adjacent carbon atoms and in which the bond axis of these adjacent carbon atoms is inhibited from rotating by bond unsaturation, e.g. aromatic, heterocyclic, olefinic, or acetylenic, or by their incorporation into an alicyclic ring system comprising a three- to eight-membered ring. When A is an alicyclic group or includes an alkylene linkage, the bidentate ligand includes cis-type and trans-type steric isomers. Included among the ligands that can be employed herein, some of which are believed to be novel, are those defined below in Table I, referring to the structural formula hereinabove defined.

TABLE I

| | $R_1$ | $R_2$ | $R_3$ | $R_4$ | $R_5$ | $R_6$ | $R_7$ | $R_8$ | $E_1$ | $E_2$ | A | m | n |
|---|---|---|---|---|---|---|---|---|---|---|---|---|---|
| 1. | Phenyl | Phenyl | Phenyl | Phenyl | — | — | — | — | P | P | H H<br>—C=C— | 0 | 0 |
| 2. | Phenyl | Phenyl | Phenyl | Phenyl | — | — | — | — | P | P |  | 0 | 0 |
| 3. | Phenyl | Phenyl | Phenyl | Phenyl | H | H | H | H | P | P |  | 1 | 1 |
| 4. | Phenyl | Phenyl | Phenyl | Phenyl | CH₃ | H | H | H | P | P |  | 1 | 1 |
| 5. | Phenyl | Phenyl | Phenyl | Phenyl | CH₃ | H | CH₃ | H | P | P |  | 0 | 0 |
| 6. | Phenyl | Phenyl | Ethyl | Ethyl | — | — | — | — | P | P |  | 0 | 0 |
| 7. | Phenyl | Phenyl | Ethyl | Ethyl | H | CH₃ | H | H | P | As |  | 1 | 1 |
| 8. | Phenyl | Phenyl | Phenyl | Phenyl | — | — | — | — | P | P |  | 0 | 0 |
| 9. | Phenyl | Phenyl | Phenyl | Phenyl | — | — | — | — | P | P |  | 0 | 0 |
| 10. | Phenyl | Phenyl | Phenyl | Phenyl | — | — | — | — | P | P |  | 0 | 0 |
| 11. | Phenyl | Phenyl | Phenyl | Phenyl | — | — | — | — | P | P |  | 0 | 0 |
| 12. | Phenyl | Phenyl | Ethyl | Ethyl | H | H | H | H | P | P |  | 1 | 1 |
| 13. | Phenyl | Phenyl | Phenyl | Phenyl | H | H | H | H | P | P |  | 0 | 0 |
| 14. | Phenyl | Phenyl | Phenyl | Phenyl | — | — | — | — | P | P | —C≡C— | 0 | 0 |
| 15. | Phenyl | Phenyl | Phenyl | Phenyl | H | H | H | H | P | P |  | 1 | 1 |

Any source of iodine which is capable of dissociating, that is, ionizing to form free iodide ions in the reaction medium, can be used in the present invention. Illustrative examples of iodine compounds especially suitable for use herein include iodine, potassium iodide, calcium iodide, sodium iodide, lithium iodide, aluminum iodide, bismuth iodide, hydrogen iodide, methyl iodide, ethyl iodide, etc., and mixtures thereof.

The cobalt entity suitable for use herein can be defined as being a cobalt carbonyl, a hydrido cobalt carbonyl or a cobalt-containing compound convertible to a cobalt carbonyl or a hydrido cobalt carbonyl. By "cobalt carbonyl" we intend to define a compound containing only cobalt and carbon monoxide, such as $Co_2(CO)_8$ or $Co_4(CO)_{12}$. By "hydrido cobalt carbonyl" we intend to define a compound containing only cobalt, carbon monoxide and hydrogen, such as $HCo(CO)_4$. By "cobalt-containing material convertible to a cobalt carbonyl or a hydrido cobalt carbonyl" we intend to define any material which when mixed with hexane and subjected to 4000 pounds per square inch gauge (27.6 MPa) in an atmosphere containing hydrogen and carbon monoxide in a molar ratio of 1:1 at 150° to 200° C. for a period of three hours will result in the formation of a cobalt carbonyl, a hydrido cobalt carbonyl or mixtures thereof. Specific examples of a cobalt-containing material so convertible to a cobalt carbonyl or a hydrido cobalt carbonyl include cobalt (II) sulfate, cobalt oxide ($Co_3O_4$), cobalt(II)tetrafluoroborate, cobalt(II)acetate, cobalt(II)oxalate, cobalt(II)propionate, cobalt(II)octoate, cobalt(II)butyrate, cobalt(II)benzoate, cobalt(II)valerate, cobalt(II)formate, cobalt(II)cyclohexanebutyrate, cobalt(II)2-ethyl-hexaoate, cobalt(II)gluconate, cobalt(II)lactate, cobalt(II)naphthenate, cobalt(II)oleate, cobalt(II)citrate, cobalt(II)acetylacetonate, etc.

Any source of ruthenium that can be converted to a ruthenium complex containing carbon monoxide under the conditions of the reaction herein and which is soluble in the reaction medium can be employed herein. Of these, mention can be made of ruthenium itself, ruthenium acetyl acetonate, ruthenium pentacarbonyl, triruthenium dodecacarbonyl, ruthenium trichloride, ruthenium tribromide, ruthenium triiodide, ruthenium acetate, ruthenium propionate, ruthenium octanoate, ruthenium oxide, ruthenium tetraoxide, etc.

The relative amounts of carbon monoxide and hydrogen employed can be varied over a wide range. However, in general, the molar ratio of carbon monoxide to hydrogen is from about 1:10 to about 5:1, preferably about 1:5 to about 3:1, but most preferably about 1:2 to about 1.5:1. Compounds or reaction mixtures which give rise to the formation of carbon monoxide and hydrogen under the reaction conditions defined herein can be used instead of mixtures comprising carbon monoxide and hydrogen which are used in the preferred embodiments of this invention.

The molar ratio of cobalt, based on the element cobalt, to the ligand can be in the range of about 10:1 to about 1:5, preferably about 4:1 to about 1:2. The molar ratio of cobalt, based on the element cobalt, to iodine, based on the element iodine, can be in the range of about 8:1 to about 1:6, preferably about 4:1 to about 1:4, but most preferably about 2:1 to about 1:2. The molar ratio of cobalt, based on the element cobalt, to ruthenium, based on the element ruthenium, can be in the range of about 1:4 to about 20:1, preferably about 1:1 to about 15:1, but most preferably about 5:1 to about 12:1. Based on the methanol introduced into the system, the weight percent of combined cobalt and iodine, in their elemental form, can range from about 0.01 to about 10 percent, preferably from about 0.1 to about five percent.

The process herein can be carried out either in a batch operation or by passing the reactants continuously through a reaction zone. In each case the reactor is provided with agitation means, and the pressure is maintained therein by the addition of hydrogen and carbon monoxide, or compounds producing hydrogen and carbon monoxide, as required. In order to facilitate the introduction of the phosphorus-containing ligand and the cobalt and iodine entities into the reaction zone and/or to facilitate recovery of the components of the reaction herein, they can be dissolved in an inert solvent, such as ethylene glycol, diethylene glycol monomethyl ether, acetone, sulfolanes, such as tetramethylene sulfone, lactones, such as $\gamma$-butyrlactone and $\epsilon$-caprolactone, etc.

In the reaction zone the contents thereof are maintained at an elevated temperature and at an elevated critical pressure for a time sufficient to convert methanol to the desired aldehydes. The total pressure (based on hydrogen, carbon monoxide and any produced gases) must be at least about 2200 pounds per square inch gauge (15.02 MPa) but need not be in excess of about 10,000 pounds per square inch gauge (68.30 MPa). Especially desirable are pressures in the range of about 2500 pounds per square inch gauge (17.07 MPa) to about 7500 pounds per square inch gauge (51.19 MPa). Temperatures which are suitable for use herein are those temperatures which initiate a reaction between the reactants herein to selectively produce alcohols generally from about 150° to about 250° C., preferably from about 170° to about 220° C. The reaction is conducted for a time period sufficient to convert methanol to alcohols, normally from about five minutes to about five hours, preferably from about ten minutes to about 2.5 hours.

Recovery of the desired ethanol from the reaction product can be effected in any convenient or conventional manner, for example, by distillation. The components will distill off in the following sequence for the desired recovery: acetaldehyde, propionaldehyde, methyl acetate, methanol, butyraldehyde, ethyl acetate, ethanol, etc.

DESCRIPTION OF PREFERRED EMBODIMENTS

A series of runs was carried out as follows:

In each of Runs Nos. 1, 2, 3 and 5, there was charged into a 300 cc. stainless steel autoclave equipped with agitation means, 100 milliliters of methanol, 10 millimols of cobaltous acetylacetonate, 1.0 millimol of ruthenium acetylacetonate, 10 millimols of iodine ($I_2$) and five millimols of a specific ligand containing atoms from Group VB of the Periodic Table separated by an unsaturated linkage. Run No. 4 was similar, except that 5.0 millimols of cobalt carbonyl were used. In all the runs, the cobalt to ligand molar ratio was 1:0.5. These ligands were as follows:

(Run No.1) cis-bis(1,2-diphenylphosphino)ethylene;
(Run No.2) bis(1,2-diphenylphosphine)benzene;
(Run No.3) bis-alpha-alpha'-diphenylphosphine)-O-oxylene; and
(Run No.5) bis(diphenylphosphino)acetylene.

The reactor was next purged twice with nitrogen gas and then pressurized with carbon monoxide and hydrogen to a pressure of about half the desired reaction pressure. The system was then heated to a temperature of 200° C. and the pressure was adjusted to 4000 pounds per square inch gauge (27.3 MPa), while maintaining a molar ratio of carbon monoxide to hydrogen of 1:1 in the reaction zone, and such pressure was maintained throughout the reaction period. At the end of the reaction period the reactor contents were cooled by an internal cooling coil to about −75° C. The reactor was vented through a dry gas meter, and a gas sample was taken for mass spectral analysis; and the liquid product was then analyzed by gas choromatography. The data obtained are set forth below in Table II.

run with ruthenium also present. Note that in the run wherein the smallest increase was obtained, Run No. 1, the increase amounted to almost six mol percent. Attention is also invited to Run No. 4 wherein about 27 mol percent ethanol was obtained in excess of the amount that would have been predicted.

TABLE II

| Run No. | Phosphorus-Containing Ligand[a] | | | | Co:I Molar Ratio | Reaction Time, Hours | Percent MeOH[b] Converted | EtOH[c] | Realizable EtOH[d] | Realizable Alcohols[e] | Others[f] |
|---|---|---|---|---|---|---|---|---|---|---|---|
| | m | n | R₅R₆R₇R₈ | A | | | | | | | |
| 1 | 0 | 0 | — | H H —C=C— | 0.5:1 | 1.5 | 83.6 | 41.7 | 75.3 | 84.9 | 15.1 |
| 2 | 0 | 0 | — |  | 0.5:1 | 1.0 | 82.0 | 52.1 | 79.5 | 87.5 | 12.5 |
| 3. | 1 | 1 | Hydrogen |  | 0.5:1 | 1.0 | 78.4 | 44.3 | 69.2 | 76.0 | 24.0 |
| 4[g] | 1 | 1 | Hydrogen |  | 0.76:1 | 1.0 | 72.0 | 51.4 | 81.6 | 82.5 | 17.5 |
| 5 | 0 | 0 | — | —C≡C— | 0.5:1 | 1.0 | 83.8 | 53.7 | 75.5 | 81.5 | 18.5 |

[a] 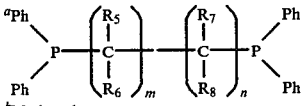
[b] Methanol
[c] Ethanol
[d] Ethanol + compounds convertible thereto = $\frac{\text{mols ethanol + mols acetaldehyde + 2(mols diethylether) + mols ethyl acetate}}{\text{total mols product}}$
[e] Total alcohols = $\frac{\text{mols realizable ethanol + mols propanal + mols butanal + mols propanol + mols butanol}}{\text{total mols product}}$
[f] Methyl formate, methyl acetate, acetic acid
[g] Cobalt carbonyl used; cobalt acetylacetonate in remaining runs The data in Table II above illustrate the advantages of operating within the strict limitations of the invention defined and claimed herein. Note that in each of the runs the amounts of ethanol, realizable ethanol and realizable alcohol were substantial and that the amounts of less desirable compounds, although valuable in themselves as chemical compounds, were relatively small.

We have found, unexpectedly, that we can obtain more ethanol in our homologated product than we would have predicted. This is shown below in Table III. A run was carried out identically to each of our five runs described above, with the exception that no ruthenium was present in the reaction system. In each of the additional runs, the homologated product was analyzed for its ethanol, acetaldehyde, dimethyl acetal, diethyl ether and ethyl acetate content. Assuming that acetaldehyde can be hydrogenated to ethanol, that dimethyl acetal can be hydrolyzed and then hydrogenated to ethanol and that diethyl ether and ethyl acetate can by hydrolyzed to ethanol, calculations were made on the total amount of ethanol that could have been produced if the homologated product were simply subjected to hydrolysis and/or hydrogenation in the presence of the ruthenium employed herein. In Table III, this is shown in the column titled "Expected Ethanol". In the next column, titled "Ethanol Obtained", there is shown the amount of ethanol in fact obtained in the corresponding

TABLE III

| | Product, Mol Percent | |
|---|---|---|
| Run No. | Expected Ethanol | Ethanol Obtained |
| 1 | 76.1 | 80.8 |
| 2 | 74.0 | 81.9 |
| 3 | 65.9 | 74.7 |
| 4 | 64.3 | 81.6 |
| 5 | 63.2 | 77.0 |

Obviously, many modifications and variations of the invention, as hereinabove set forth, can be made without departing from the spirit and scope thereof, and therefore only such limitations should be imposed as are indicated in the appended claims.

We claim:

1. A process for selectively producing ethanol which comprises introducing into a reaction zone (1) methanol, (2) carbon monoxide, (3) hydrogen, (4) cobalt, (5) iodine, (6) ruthenium and (7) a ligand containing atoms selected from the group consisting of nitrogen, phosphorus and arsenic separated by a sterically constrained carbon-carbon bond, the molar ratio of carbon monoxide to hydrogen being in the range of about 1:10 to about 5:1; the molar ratio of cobalt to said ligand being in the range of about 10:1 to about 1:5; the molar ratio of cobalt to iodine being in the range of about 8:1 to about 1:6; the molar ratio of cobalt to ruthenium being in the range of about 1:4 to about 20:1; and the weight percent of combined cobalt and iodine, based on the methanol, being in the range of about 0.01 to about ten percent; and then subjecting said contents to an elevated temperature of about 150° to about 250° C. and an elevated pressure of at least about 2200 pounds per square inch for about five minutes to about five hours, sufficient to convert methanol to a product predominating in ethanol.

2. The process of claim 1 wherein each of said atoms is phosphorus.

3. The process of claim 1 wherein each of said atoms is arsenic.

4. The process of claim 1 wherein one of said atoms is phosphorus and another is arsenic.

5. The process of claim 1 wherein said sterically constrained carbon-carbon bond can be an alkenylene bond, a 1,2-arylene bond or an acetylenic bond.

6. The process of claim 1 wherein said sterically constrained carbon-carbon bond is an alkenylene bond.

7. The process of claim 1 wherein said sterically constrained carbon-carbon bond is a 1,2-arylene bond.

8. The process of claim 1 wherein said sterically constrained carbon-carbon bond is an acetylenic bond.

9. The process of claim 1 wherein said sterically constrained bond is incorporated into an alicyclic ring system.

10. The process of claim 1 wherein the molar ratio of carbon monoxide to hydrogen is in the range of about 1:5 to about 3:1; the molar ratio of cobalt to said ligand is in the range of about 4:1 to about 1:2; the molar ratio of cobalt to iodine is in the range of about 4:1 to about 1:4; and the weight percent of combined cobalt and iodine, based on the methanol, is in the range of about 0.1 to about five percent; and then subjecting said contents to an elevated temperature of about 170° to about 220° C. and an elevated pressure of about 2500 to about 7500 pounds per square inch gauge for about ten minutes to about 2.5 hours, sufficient to convert methanol to a product predominating in alcohols.

11. The process of claim 10 wherein the molar ratio of carbon monoxide to hydrogen is in the range of about 1:2 to about 1.5:1, the cobalt to iodine molar ratio is in the range of about 2:1 to about 1:2; and the cobalt to ruthenium molar ratio is in the range of about 5:1 to about 12:1.

12. The process of claim 1 wherein the ligand is defined by the following formula:

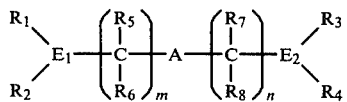

wherein $R_1$, $R_2$, $R_3$ and $R_4$ are either alike or different members selected from the group consisting of alkyl radicals having from one to 24 carbon atoms, aryl radicals having from six to 20 carbon atoms, alkenyl radicals having from two to 30 carbon atoms, cycloalkyl radicals having from three to 40 carbon atoms, and aralkyl and alkaryl radicals having from six to 40 carbon atoms; $R_5$, $R_6$, $R_7$ and $R_8$ are either alike or different members selected from the group consisting of hydrogen alkyl radicals having from one to 24 carbon atoms, aryl radicals having from six to 20 carbon atoms, alkenyl radicals having from two to 30 carbon atoms, cycloalkyl radicals having from three to 40 carbon atoms, and aralkyl and alkaryl radicals having from six to 40 carbon atoms; $E_1$ and $E_2$ are atoms selected from the group consisting of nitrogen, phosphorus and arsenic; A is an organic divalent radical in which the radical centers are located on adjacent carbon atoms and in which the bond axis of these adjacent carbon atoms is inhbited from rotating by bond unsaturation; and m and n are integers ranging from 0 to 2, provided that m+n is equal to 0 to 4.

13. The process of claim 12 wherein $R_1$, $R_2$, $R_3$ and $R_4$ are either alike or different members selected from the group consisting of alkyl radicals having from two to ten carbon atoms, aryl radicals having from six to ten carbon atoms, alkenyl radicals having from two to 20 carbon atoms, cycloalkyl radicals having from three to 30 carbon atoms, and aralkyl and alkaryl radicals having from six to 30 carbon atoms; $R_5$, $R_6$, $R_7$ and $R_8$ are either alike or different members selected from the group consisting of hydrogen, alkyl radicals having from two to ten carbon atoms, aryl radicals having from six to ten carbon atoms, alkenyl radicals having from two to 20 carbon atoms, cycloalkyl radicals having from three to 30 carbon atoms, and aralkyl and alkaryl radicals having from six to 30 carbon atoms; and $E_1$ and $E_2$ can be nitrogen, phosphorus or arsenic.

14. The process of claim 12 wherein $E_1$ and $E_2$ are phosphorus.

15. The process of claim 12 wherein $E_1$ and $E_2$ are arsenic.

16. The process of claim 12 wherein $E_1$ is phosphorus and $E_2$ is arsenic.

17. The process of claim 12 wherein said bond unsaturation has from two to ten carbon atoms.

18. The process of claim 12 wherein said bond unsaturation has from two to six carbon atoms.

19. The process of claim 12 wherein said bond unsaturation is an alkenylene bond.

20. The process of claim 12 wherein said bond unsaturation is a 1,2-arylene bond.

21. The process of claim 12 wherein said bond unsaturation is an acetylenic bond.

22. The process of claim 12 wherein said bond unsaturation is incorporated into an alicyclic ring system.

23. The process of claim 12 wherein $R_1$, $R_2$, $R_3$ and $R_4$ can be aryl or alkyl radicals.

24. The process of claim 12 wherein $R_1$, $R_2$, $R_3$ and $R_4$ are aryl radicals.

25. The process of claim 12 wherein $R_1$, $R_2$, $R_3$ and $R_4$ are alkyl radicals.

26. The process of claim 13 wherein $R_1$, $R_2$, $R_3$ and $R_4$ are aryl or alkyl radicals.

27. The process of claim 13 wherein $R_1$, $R_2$, $R_3$ and $R_4$ are aryl radicals.

28. The process of claim 13 wherein $R_1$, $R_2$, $R_3$ and $R_4$ are alkyl radicals.

29. The process of claim 13 wherein $R_5$, $R_6$, $R_7$ and $R_8$ can be hydrogen or aryl or alkyl radicals.

30. The process of claim 13 wherein $R_5$, $R_6$, $R_7$ and $R_8$ are hydrogen.

31. The process of claim 13 wherein $R_5$, $R_6$, $R_7$ and $R_8$ are aryl radicals.

32. The process of claim 13 wherein $R_5$, $R_6$, $R_7$ and $R_8$ are alkyl radicals.

33. The process of claim 13 wherein $R_1$, $R_2$, $R_3$ and $R_4$ are phenyl radicals, and $R_5$, $R_6$, $R_7$, and $R_8$ are hydrogen.

34. The process of claim 12 wherein m and n are equal to 0; $R_1$, $R_2$, $R_3$ and $R_4$ are phenyl; and A is ethylene.

35. The process of claim 13 wherein m and n are equal to 0; $R_1$, $R_2$, $R_3$ and $R_4$ are phenyl; and A is ethenylene.

36. The process of claim 12 wherein m and n are equal to 0; $R_1$, $R_2$, $R_3$ and $R_4$ are phenyl; and A is 1,2-phenylene.

37. The process of claim 13 wherein m and n are equal to 0; $R_1$, $R_2$, $R_3$ and $R_4$ are phenyl; and A is 1,2-phenylene.

38. The process of claim 12 wherein m and n are equal to 1; $R_1$, $R_2$, $R_3$ and $R_4$ are phenyl; $R_5$, $R_6$, $R_7$ and $R_8$ are hydrogen; and A is 1,2-phenylene.

39. The process of claim 13 wherein m and n are equal to 1; $R_1$, $R_2$, $R_3$ and $R_4$ are phenyl; $R_5$, $R_6$, $R_7$ and $R_8$ are hydrogen; and A is 1,2-phenylene.

40. The process of claim 12 wherein m and n are equal to 0; $R_1$, $R_2$, $R_3$ and $R_4$ are phenyl; and A is acetylene.

41. The process of claim 12 wherein m and n are equal to 0; $R_1$, $R_2$, $R_3$ and $R_4$ are phenyl; and A is acetylene.

* * * * *